United States Patent [19]
Hommeltoft

[11] Patent Number: 5,942,654
[45] Date of Patent: Aug. 24, 1999

[54] PROCESS FOR THE REMOVAL OF CORROSIVE COMPOUNDS FROM A FLUID STREAM

[75] Inventor: Sven Ivar Hommeltoft, Hillerød, Denmark

[73] Assignee: Haldor Topsoe A/S, Lyngby, Denmark

[21] Appl. No.: 08/874,702

[22] Filed: Jun. 13, 1997

[30] Foreign Application Priority Data

Jun. 17, 1996 [DK] Denmark .................................. 0669/96

[51] Int. Cl.⁶ ................................ C07C 2/58; C07C 2/66; C07C 7/10
[52] U.S. Cl. .......................... 585/720; 585/464; 585/712; 585/723; 585/730; 585/731; 585/834; 585/835; 585/836; 585/838; 585/839; 585/950; 208/47
[58] Field of Search ...................................... 585/712, 723, 585/730, 833, 834, 835, 836, 838, 839, 950, 458, 462, 464, 720; 208/47

[56] References Cited

U.S. PATENT DOCUMENTS 5,220,095 6/1993 Hommeltoft et al. .................... 585/720
5,245,100 9/1993 Hommeltoft et al. .................... 585/720

*Primary Examiner*—Bekir L. Yildirim
*Attorney, Agent, or Firm*—Ostrolenk, Faber, Gerb & Soffen, LLP

[57] ABSTRACT

A process for the removal of corrosive compounds from a fluid stream, comprising the steps of: in an extraction column with an outer steel tube and an inner tube of corrosion resistant material having an open inlet end and an open outlet end and being arranged coaxially with and spaced apart within at least top portion of the outer tube, introducing at elevated temperature at the inlet end of the inner tube the fluid stream and an extraction agent and effecting in the mixed stream of the fluid and extraction agent extraction of the corrosive compounds; introducing into an annular space between the walls of the outer and the inner tube a shell stream of a non-corrosive fluid, thereby absorbing in the shell stream amounts of the corrosive compounds diffusing through the wall of the inner tube; passing the shell stream to the bottom portion of the outer tube; cooling the mixed stream at the outlet end of the inner tube by introducing into the stream a cooling stream; passing the cooled stream to the bottom portion of the outer tube and combining the stream with the shell stream; withdrawing from the bottom portion of the outer tube an effluent stream of the combined cooled stream and the shell stream and cooling the effluent stream; and recovering from the remaining portion of the cooled effluent stream an extracted fluid stream.

1 Claim, 1 Drawing Sheet

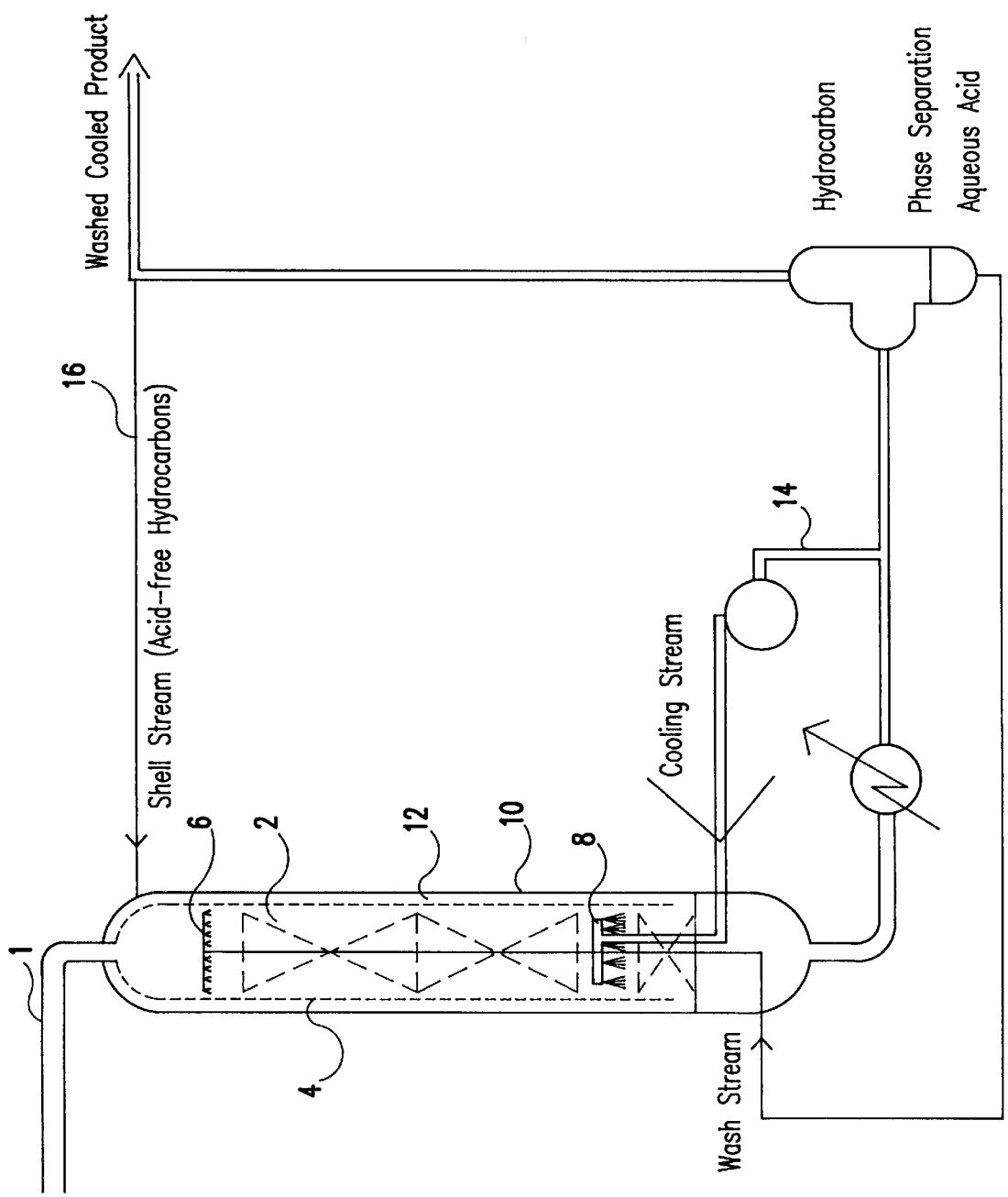

PROCESS FOR THE REMOVAL OF CORROSIVE COMPOUNDS FROM A FLUID STREAM

FIELD OF THE INVENTION

The present invention relates to the removal of corrosive compounds from a fluid stream by extraction of the stream with an extraction agent at elevated temperatures.

BACKGROUND OF THE INVENTION

Removal of corrosive compounds from fluids is typically performed in large scale processes by absorption of the compounds in an extraction agent. To avoid serious corrosion problems and to improve lifetime of the equipment, the equipment used in those processes has to be protected by lining materials of corrosive resistant material.

Lining materials frequently employed in extraction vessels are vitreous glass or polymeric materials including teflon, PFA, PVDF and the like.

Though the lining material is able to withstand corrosive attack at elevated operation temperatures, problems occur frequently when the corrosive compounds permeate through the liner to the surrounding steel walls of the equipment.

Reactors for use in the extraction process consisting solely of liner material without a stabilizing steel support will not be sufficiently mechanical stable to withstand the operation pressure typically employed during industrial extraction processes.

As a consequence, treatment of corrosive fluids requires expansive alloys for process equipment and piping.

Thus, it is the general object of this invention to provide a process for the removal of corrosive compounds from a fluid stream by which process contact between the corrosive compounds and steel construction material is avoided at high temperatures, which otherwise causes severe corrosion on the construction material.

SUMMARY OF THE INVENTION

In accordance with the present invention, a process for the removal of corrosive compounds from a fluid stream, comprising the steps of:

in an extraction column with an outer steel tube and an inner tube of permeable corrosion resistant material having an open inlet end and an open outlet end and being arranged coaxially with and spaced apart within at least top portion of the outer tube, introducing at elevated temperature at the inlet end of the inner tube the fluid stream and an extraction agent and effecting in the mixed stream of the fluid and extraction agent extraction of the corrosive components;

introducing into an annular space being formed between wall of the outer and the inner tube a shell stream of a non-corrosive fluid and thereby absorbing in the shell stream amounts of the corrosive compounds diffusing through the wall of the inner tube; and passing the shell stream to bottom portion of the outer tube;

cooling the mixed stream at the outlet end of the inner tube by introducing into the stream a cooling stream;

passing the cooled stream to the bottom portion of the outer tube and combining the stream with the shell stream;

withdrawing from the bottom portion of the outer tube an effluent stream of the combined cooled stream and the shell stream and cooling the effluent stream;

recovering from the remaining portion of the cooled effluent stream an extracted fluid stream.

Preferably, the coling stream being used to cool the mixed stream at outlet end of the inner tube is obtained by circulating back a portion of the cooled effluent stream to the outlet end of the inner tube.

The extracted fluid stream will conveniently be recovered by phase separation of the effluent stream.

DESCRIPTION OF THE INVENTION

In the following description various aspects and features of the invention are disclosed in more detail by reference to the drawing in which the sole figure shows a simplified flow sheet of a specific embodiment of the inventive process for the removal of acidic corrosive compounds in a product stream from acid catalyzed alkylation of hydrocarbons.

In the removal of the acid in the hydrocarbon stream by extraction with hot water or aqueous acid causes corrosive attack of the aqueous acid on steel equipment, which is highly sensitive to corrosion at elevated temperature.

By the process of this invention, direct physical contact between the hot corrosive medium and the construction steel of the contact vessel is avoided.

Acid present in the effluent stream (as dissolved free acid or as acid derivatives such as esters) from acid catalyzed hydrocarbon conversion processes such as isobutane alkylation can be removed by washing with water. The efficiency of the washing step is increased when the process is conducted at elevated temperature (50–200° C.). However, the diluted aqueous acid formed in the extraction process becomes increasingly more corrosive for construction steels as the temperature increases. As a consequence, more expensive alloys are required for the equipment and piping.

Referring to the FIGURE, a hot acid containing hydrocarbon stream 1 is treated in an extraction vessel according to the invention by passing the stream 1 into packed bed 2 in inner tube 4 constructed of permeable corrosion resistant material. Water is added through distributor 6 to the stream. After having been passed further through the bed, the mixed hot stream is mixed with cooling stream 8 in such way that the mixed stream is cooled before leaving the portion of the packed bed which is surrounded by the inner tube. Cooling stream 14 may preferably be a cooled effluent stream from the process. In this way the mixed stream is cooled before it comes into contact with outer steel tube 10 surrounding the inner tube. Diluted aqueous acid is separated from the cooled washed hydrocarbon stream and a portion 16 substantially of the acid free stream is used to flush annular space 12 between inner tube 4 and the steel-walls of outer tube 10. Thereby, corrosive components diffusing through inner tube 4 are flushed away, which also prevents the stream leaving the open end of the inner tube from flowing back along the outside of the inner tube to the hot region of the vessel, where it could otherwise cause corrosion.

A stream comprising a reagent, which substantially lowers the corrosiveness of the medium may also be added further to reduce the corrosion of the stream. In case of removal of acidic components from a hydrocarbon process stream by wash with water, such reagent may be an-alkaline material, which neutralizes the acid.

EXAMPLE 1

Effect of temperature on removal of trifluromethanesulphonic acid from an alkylated hydrocarbon product stream.

The process equipment used in this Example was the same as illustrated in the FIGURE. Alkylate having a total content of trifluromethanesulphonic acid (TfOH) of 33 ppm (w/w) as produced by isobutane alkylation using triflurome-hanesulphonic acid as catalyst as further described in U.S. Pat. Nos. 5,220,095 and 5,245,100. The raw product was mixed with water at a ratio of about ⅕ and passed through a ⅛" Hasteloy steel tube submerged in an oil bath (submerged volume: approx. 6 ml), and then through a water bath to be cooled before the stream passes through a back pressure valve used to control the pressure. The pressure was maintained at 15–20 bars. Table 1 summarizes the reaction conditions together with the acid contents found in the alkylate after the treatment.

TABLE 1

| Temp °C. | Residence time minutes | TfOH in product ppm(w/w) | TfOH removal % |
|---|---|---|---|
| 100 | 2.4 | 7 | 78 |
| 140 | 2.5 | 2.6 | 92 |
| 160 | 2.2 | 3.2 | 90 |
| 160 | 2.4 | 1.2 | 96 |
| 177 | 2.4 | 0.4 | 99 |
| 195 | 2.5 | <0.3 | >99 |

EXAMPLE 2

Temperature dependence of corrosion rates.

Samples of 316 L stainless steel tubing were weighed and submerged in dilute aqueous trifluromethanesulphonic acid at different temperatures between 25–150° C. for a period of 5 to 7 days. Each sample was then washed with water, dried and weighed again. Corrosion rate was calculated from weight loss by assuming an even corrosion over the entire surface of each steel piece.

Following corrosion rates were calculated for 316 L:

TABLE 2

| Medium | Temperature °C. | Corrosion rate mm/year |
|---|---|---|
| 5% $CF_3SO_3H$ in $H_2O$ | 25 | 0.005 |
| 3% $CF_3SO_3H$ in $H_2O$ | 103 | 0.5 |
| 5% $CF_3SO_3H$ in $H_2O$ | 155 | 5.7 |

I claim:
1. Process for the removal of corrosive compounds from a fluid stream, comprising the steps of:
in an extraction column with an outer steel tube and an inner tube of permeable corrosion resistant material having an open inlet end and an open outlet end and being arranged coaxially with and spaced apart within at least top portion of the outer tube, introducing at elevated temperature at the inlet end of the inner tube the fluid stream and an extraction agent for the corrosive compounds and effecting in the mixed stream of the fluid and extraction agent extraction of the corrosive components;
introducing into an annular space between the walls of the outer and the inner tube a shell stream of a non-corrosive fluid and thereby absorbing in the shell stream amounts of the corrosive compounds diffusing through the wall of the inner tube;
passing the shell stream to bottom portion of the outer tube;
cooling the mixed stream at the outlet end of the inner tube by introducing into the stream a cooling stream;
passing the cooled stream to the bottom portion of the outer tube and combining the stream with the shell stream;
withdrawing from the bottom portion of the outer tube an effluent stream of the combined cooled stream and the shell stream and cooling the effluent stream; and
recovering from the remaining portion of the cooled effluent stream an extracted fluid stream;
wherein the fluid stream introduced into the extraction column comprises a product stream from acid catalyzed alkylation of hydrocarbons and the corrosive compounds comprise an acid alkylation catalyst.

\* \* \* \* \*